United States Patent [19]

Hofstetter

[11] 4,317,903

[45] Mar. 2, 1982

[54] PROCESS FOR THE PURIFICATION OF LINCOMYCIN

[75] Inventor: John R. Hofstetter, Kalamazoo, Mich.

[73] Assignee: The Upjohn Company, Kalamazoo, Mich.

[21] Appl. No.: 228,396

[22] Filed: Jan. 26, 1981

[51] Int. Cl.$^3$ ............................................. C07H 15/16
[52] U.S. Cl. ...................................................... 536/11
[58] Field of Search ........................................... 536/11

[56] References Cited

U.S. PATENT DOCUMENTS 3,544,552 12/1970 Argoudelis et al. ................... 536/11
3,907,774 9/1975 Argoudelis et al. ................... 536/11

OTHER PUBLICATIONS

Brown, "Jour. Pharm. Sci.," vol. 67, No. 9, Sep. 1978, pp. 1254–1257.

*Primary Examiner*—Johnnie R. Brown
*Attorney, Agent, or Firm*—Roman Saliwanchik

[57] ABSTRACT

A recovery process, using a reverse-phase high performance preparative liquid chromatography (hpplc) which gives a highly pure preparation of the useful antibiotic lincomycin hydrochloride. While giving a highly pure preparation of lincomycin hydrochloride, wherein less than about 0.5% of lincomycin B hydrochloride is present, the process also yields analytically pure lincomycin B hydrochloride which can be used as a laboratory standard.

6 Claims, No Drawings

PROCESS FOR THE PURIFICATION OF LINCOMYCIN

DESCRIPTION

BACKGROUND OF THE INVENTION

Lincomycin, initially known as lincolnensin, is a useful antibiotic. Procedures for preparing the antibiotic are disclosed in U.S. Pat. No. 3,086,912. Lincomycin fermentations yield the desired lincomycin (lincomycin A), and the compound lincomycin B. Lincomycin sold for medicinal use must not contain more than about 4% lincomycin B. Thus, there is a constant search for recovery procedures which can be used to achieve this goal in the most effective manner.

The publication "High-Pressure Liquid Chromatographic Assays for Clindamycin, Clindamycin Phosphate, and Clindamycin Palmitate" in Jour. of Pharm. Sciences, Vol. 67, No. 9, Sept. 1978, pp. 1254–1257, discloses an assay procedure which can not be used as a recovery process. The starting material used in the assay is pure material as contrasted with the impure material used in the subject invention process. Most importantly, the assay procedure uses paired ion chromatography. This can not be used in a recovery process because the paired ion goes into the desired product, and can be separated therefrom, if at all, only with great difficulty.

The process described herein is considered to be the best known process for obtaining highly pure lincomycin hyrochloride. As an added bonus, the process also yields analytically pure preparations of lincomycin B hydrochloride which can be used as a laboratory standard.

BRIEF SUMMARY OF THE INVENTION

Upon subjecting an impure preparation comprising lincomycin and lincomycin B to a reverse-phase high performance preparative liquid chromatography (hpplc), there are obtained a preparation of lincomycin hydrochloride (lincomycin A) containing less than about 0.5% lincomycin B, and analytically pure lincomycin B hydrochloride.

DETAILED DESCRIPTION OF THE INVENTION

The subject process for recovering lincomycin hydrochloride from a preparation comprising lincomycin hydrochloride and lincomycin B hydrochloride can be outlined by the following steps:

A. Dissolve ~450 g of the starting material per liter of 30% aqueous methanol.

B. Apply the solution to a chromatography column filled with 18 g of $C_{18}$ bonded phase silica gel per gram of starting material at 20 bed volumes per hour, and develop the chromatography with 4 bed volumes of 30% aqueous methanol.

C. Strip the remaining lincomycin from the column with 1 bed volume of methanol.

D. Concentrate the lincomycin-rich eluate to dryness.

E. Crystallize the lincomycin according to standard crystallization procedure.

F. Rechromatograph the lincomycin B-rich fraction according to the procedure outlined above.

G. Concentrate the eluate containing >98% of lincomycin B to dryness.

H. Redissolve the solids in 3 ml of methanol per gram of lincomycin B solids at 40° C., adjust the pH with concentrated hydrochloric acid to 1.5, add 7 ml of dry ethyl acetate per gram of lincomycin B, and cool the mixture slowly to 4° C. to crystallize it.

Steps A, B, C, and H can be varied as follows:

Step A—The feed solution concentration is near the practical limit. At concentrations higher than that indicated the viscosity becomes prohibitively high. A concentration range of about 300 g/l to about 450 g/l can be used.

Step B—The solids to silica ratio is near optimum as stated, but ethanol and acetonitrile can be satisfactorily substituted for the methanol in the mobile phase. Furthermore, other bonded-phase silica gels can be substituted for the $C_{18}$ if appropriate changes are made in the polarity of the mobile phase.

Step C—The necessity of this step is determined by the starting material purity.

Step H—Ethanol can be substituted for methanol in this step as well. The crystal yields depend not only on the lincomycin B concentration in the alcohol, but also on the amount of ethyl acetate added. Other esters can be used for the crystallization if the amounts used produce the same final polarity index as the methanol: ethyl acetate system.

The following examples are illustrative of the process of the invention, but are not to be construed as limiting. All percentages are by weight and all solvent mixture proportions are by volume unless otherwise noted.

EXAMPLE 1

HPPLC of Lincomycin Salvage Mother Liquors (ML)

Lincomycin salvage mother liquor, containing ca. 30% lincomycin B, and the ratio of lincomycin B to lincomycin A is about 3 to 2, is the starting material. This material is subjected to the process outlined supra. The lincomycin B eluted between about five and six column void volumes, the lincomycin A eluted next between 6 and 8.5 column void volumes, and the bulk of the colored solids eluted with the methanol wash. Yield: about 64 g of crystalline lincomycin B, and ca. 40 g of highly pure lincomycin A. The above procedure is shown in Chart 1.

EXAMPLE 2

HPPLC of Lincomycin Crude Crystalline (CC) Preparation

A crude crystalline lincomycin A preparation contained 20% of lincomycin B; the remaining solid material was primarily A. This starting material is used for twenty 18 g runs over two Prep PAK $C_{18}$ cartridges eluted isocratically with (2:1) water-methanol. Pool cuts are made. The B rich pool is concentrated to an aqueous to which enough methanol is added to make a mobile phase; this is reinjected into the Prep 500. Rich eluent from the second hpplc is concentrated as before and rechromatographed a third time. Yield: 24 g of ~99% pure lincomycin B and ca. 125 g of highly pure lincomycin A. The entire isolation scheme is outlined in Chart 2.

EXAMPLE 3

Comparison of Silica HPPLC with Reverse Phase HPPLC

Chart 3 contains a comparison of some characteristics of the silica hpplcs with those of the reverse phase hpplcs. The important differences are the following: the capacity of the stationary phases, the amount of solvent each isolation required, the time each run takes, the number of identical runs possible on the Prep PAK cartridges before the resolution deteriorated, and finally, the purity of the starting materials. Since the reverse phase column packing material can be cleaned, "dirty" starting material can be used, and the packing can be used repeatedly. Further, the solvents for this reverse phase system are, usually, nonflammable, and the solvent volumes required low. In summary, reverse phase hpplc seems to be an effective, fast, safe, and relatively low cost method of producing lincomycin B from starting materials in which lincomycin B is a minor part of the total solids, and also preparing high purity lincomycin A HCl.

CHART 1
Flow Chart of Lincomycin A and B Isolation from ML

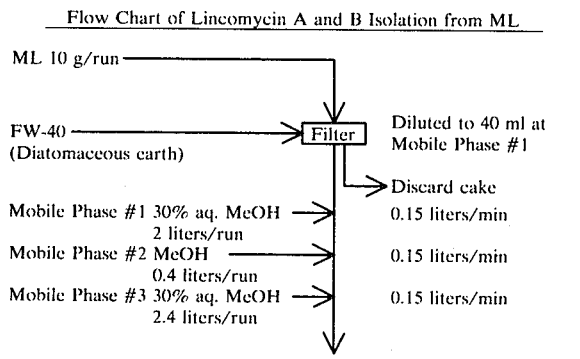
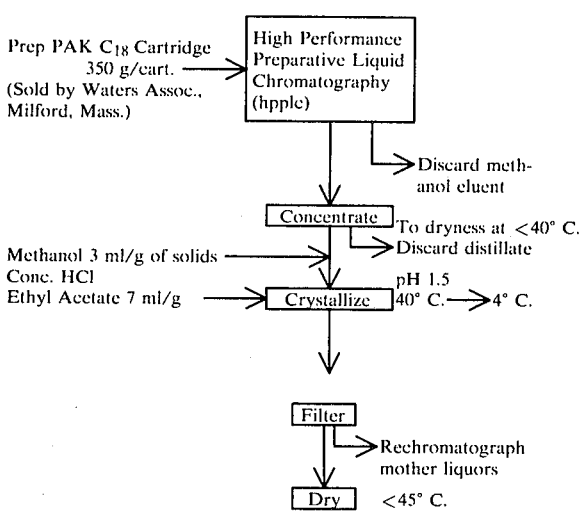

CHART 2
Flow Chart of Lincomycin A and B Isolation from CC

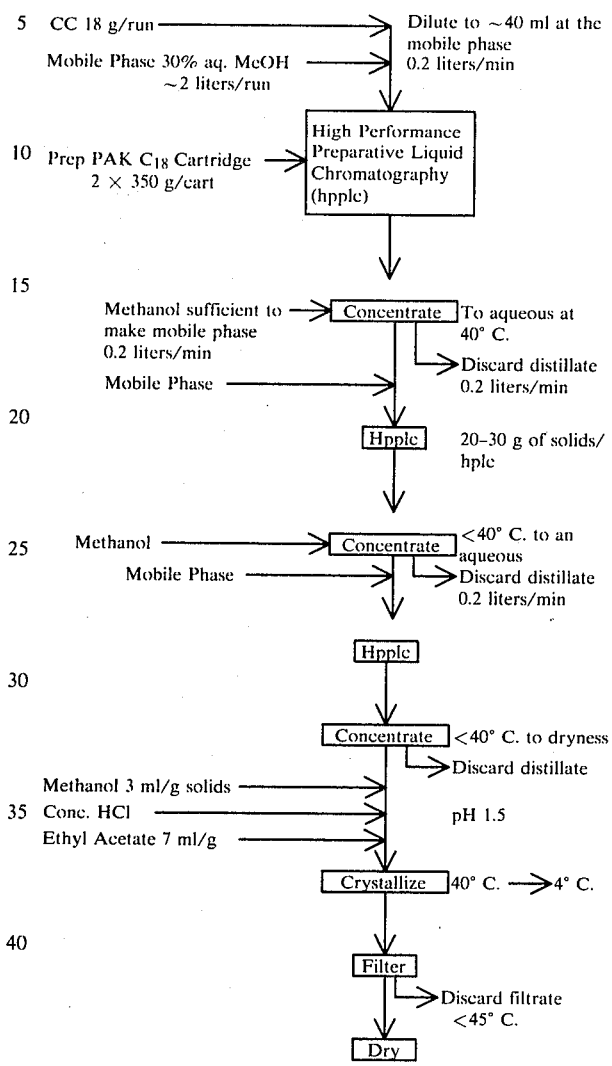

CHART 3

| | Lincomycin HPPLC: Comparison of Normal and Reversed Phase Modes | |
|---|---|---|
| | Stationary Phase | |
| Item | Silica | $C_{18}$ Bonded Silica |
| Starting Materials (S.M.) | Crude Crystalline Lincomycin A (CC) | Salvage Mother Liquors (ML) or Crude Crystalline Lincomycin (CC) |
| % B in S.M. | 14–20 | 25–35 or 14–20 |
| Solvent System | Methyl Ethyl Ketone, Acetone, Water | Water, Methanol then Methanol |
| Type of Elution Program | Isocratic | Step Gradient or Isocratic |
| Run Time (minutes) | 40–60 | 20–25 |
| Volume of Sovent Needed (l) | >10 | 2–4 |
| Loading, g silica/ g S.M. | 180 | 35 |
| Runs/Prep PAK Cartridge | 2–3 | >100 |
| Purity of Rich Eluate (%) | 40–50 | 93–97 |

CHART 3-continued

| | Lincomycin HPPLC: Comparison of Normal and Reversed Phase Modes | |
|---|---|---|
| | Stationary Phase | |
| Item | Silica | $C_{18}$ Bonded Silica |
| Yield | ~27 | ~30 |

I claim:

1. A process for recovering highly pure lincomycin hydrochloride from an impure preparation comprising lincomycin A and lincomycin B which comprises (a) subjecting said impure preparation to a reverse-phase high performance preparative liquid chromatography using a bonded-phase silica gel, and (b) recovering highly pure lincomycin hydrochloride.

2. A process, according to claim 1, wherein said bonded-phase silica gel is $C_{18}$ bonded phase silica gel.

3. A process, according to claim 1, wherein said chromatography column is developed with a solvent selected from the group consisting of methanol, ethanol and acetonitrile.

4. A process for recovering analytically pure lincomycin B hydrochloride from an impure preparation comprising lincomycin A and lincomycin B which comprises (a) subjecting said impure preparation to a reverse-phase high performance preparative liquid chromatography using a bonded-phase silica gel, and (b) recovering analytically pure lincomycin B hydrochloride.

5. A process, according to claim 4, wherein said bonded-phase silica gel is $C_{18}$ bonded phase silica gel.

6. A process, according to claim 4, wherein said chromatography column is developed with a solvent selected from the group consisting of methanol, ethanol and acetonitrile.

* * * * *